United States Patent
Baba (10) Patent No.: US 9,427,341 B2
(45) Date of Patent: Aug. 30, 2016

(54) STENT (71) Applicant: TERUMO KABUSHIKI KAISHA, Shibuya-ku (JP)

(72) Inventor: Takeshi Baba, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 89 days.

(21) Appl. No.: 14/478,025

(22) Filed: Sep. 5, 2014

(65) Prior Publication Data
US 2014/0379063 A1   Dec. 25, 2014

Related U.S. Application Data (63) Continuation of application No. PCT/JP2013/055450, filed on Feb. 28, 2013.

(30) Foreign Application Priority Data

Mar. 8, 2012 (JP) .................. 2012-051528

(51) Int. Cl.
*A61F 2/90* (2013.01)
*A61F 2/82* (2013.01)
*A61L 31/02* (2006.01)
(Continued)

(52) U.S. Cl.
CPC . *A61F 2/90* (2013.01); *A61F 2/82* (2013.01); *A61L 31/022* (2013.01); *A61L 31/14* (2013.01); *A61L 31/18* (2013.01); *C22C 19/00* (2013.01); *C22C 19/03* (2013.01); *C22C 19/07* (2013.01); *C22C 27/02* (2013.01); *C22C 27/025* (2013.01); *C22C 27/04* (2013.01); *C22C 38/00* (2013.01); *C22C 38/18* (2013.01);
(Continued)

(58) Field of Classification Search
CPC .............. A61F 2/915; A61F 2250/098; A61F 2250/043; A61F 2/82; A61F 2/90; A61L 31/18; C22C 19/07; C22C 27/02; C22C 27/04
See application file for complete search history.

(56) References Cited

U.S. PATENT DOCUMENTS 6,402,777 B1   6/2002  Globerman et al.
2001/0001317 A1   5/2001  Duerig et al.
(Continued)

FOREIGN PATENT DOCUMENTS

JP   2002-263195 A   9/2002
JP   2003-260142 A   9/2003
(Continued)

OTHER PUBLICATIONS

International Search Report (PCT/ISA/210) mailed on Apr. 16, 2013, by the Japanese Patent Office as the International Searching Authority for International Application No. PCT/JP2013/055450.
(Continued)

*Primary Examiner* — David Isabella
*Assistant Examiner* — Suba Ganesan
(74) *Attorney, Agent, or Firm* — Buchanan Ingersoll & Rooney PC (57) ABSTRACT

A stent and method of exhibiting radiopaque properties in a stent are disclosed, which includes a stent main body that is made of a metal, and a radiopaque marker that is made of a complete solid solution alloy having a corrosion potential of ±200 mV of a corrosion potential of the metal of the stent main body.

17 Claims, 4 Drawing Sheets

(51) Int. Cl.
*A61L 31/18* (2006.01)
*C22C 19/00* (2006.01)
*C22C 19/03* (2006.01)
*C22C 19/07* (2006.01)
*C22C 27/02* (2006.01)
*C22C 27/04* (2006.01)
*C22C 38/18* (2006.01)
*C22C 38/00* (2006.01)
*A61L 31/14* (2006.01)

(52) U.S. Cl.
CPC ............... *A61F 2250/0043* (2013.01); *A61F 2250/0098* (2013.01); *A61L 2400/00* (2013.01); *Y10T 29/49826* (2015.01)

(56) References Cited

U.S. PATENT DOCUMENTS

| | | |
|---|---|---|
| 2004/0127972 A1 | 7/2004 | Kitaoka et al. |
| 2004/0236409 A1* | 11/2004 | Pelton ..................... A61F 2/91 623/1.18 |
| 2005/0125052 A1 | 6/2005 | Iwata et al. |
| 2012/0123525 A1* | 5/2012 | Kramer-Brown ....... A61L 31/18 623/1.34 |

FOREIGN PATENT DOCUMENTS

| | | |
|---|---|---|
| JP | 2004-121342 A | 4/2004 |
| JP | 2004-290279 A | 10/2004 |
| JP | 2004-358242 A | 12/2004 |
| JP | 2005-278993 A | 10/2005 |

OTHER PUBLICATIONS

Shih Chun-Che, et al., "Galvanic current induced by heterogeneous structures on stainless steel wire", Corros Sci., 2005 (month unknown), vol. 47, No. 9, pp. 2199-2212.

* cited by examiner

//  STENT

CROSS-REFERENCES TO RELATED APPLICATIONS

This application is a continuation of International Application No. PCT/JP2013/055450 filed on Feb. 28, 2013, and claims priority to Japanese Application No. 2012-051528 filed on Mar. 8, 2012, the entire contents of both which are incorporated herein by reference in their entries.

TECHNICAL FIELD

The present disclosure generally relates to a stent to be placed in a living body, and more particularly to a stent having a marker which secures a high radiopaque property and can help prevent galvanic corrosion from occurring.

BACKGROUND DISCUSSION

Hitherto, on account of its low aggressiveness to patients, medical treatment has been performed by operations, for example, such as percutaneous transluminal coronary angioplasty (PTCA) and the like to a stenosed part of the coronary artery for angina pectoris, myocardial infarction and the like and by operations, for example such as percutaneous transluminal angioplasty (PTA) and the like to a stenosed part for ischemic disease and the like of the femoral artery and the carotid artery.

These methods of treatment are techniques to secure and resume the flowing of blood by widening a stenosed or occluded blood vessel using a catheter equipped with a balloon which is compactly folded at a distal end of the catheter.

In order to help prevent the widened blood vessels from becoming stenosed or occluded again, a treatment of placing a metallic stent in a blood vessel and securing patency of the blood vessel has been performed.

Generally, a stent is cut from a metallic pipe or has a mesh shape, a coil shape or the like made of a metallic wire. However, every stent has a tubular structure of which a diameter can be decreased, and is inserted into a blood vessel through a catheter while having its diameter in a decreased state, thereby expanding in diameter and being placed in a stenosed part so as to mechanically support a lumen in the blood vessel.

There is a stent in which a radiopaque metallic material is provided at the end portion of the stent as a marker so as to be able to favorably confirm a position of the stent through radioscopy.

Incidentally, each metal has a unique electric potential.

When metals of different types are brought into contact with each other and are immersed in an electrolyte solution, a potential difference (galvanic potential) can be generated between a less-noble metal (metal having greater ionization tendency) and a noble metal (metal having smaller ionization tendency) due to a difference in electric potential therebetween so that a battery (local battery, galvanic battery) is formed, and a current (local current) flows, thereby causing corrosion.

Such corrosion which is caused by an electrochemical reaction resulting from forming of the local battery having the dissimilar metals as electrodes can be referred to as galvanic corrosion, dissimilar metal contact corrosion or local current corrosion.

As a metallic material constituting a stent, stainless steel (for example, SS316L), a cobalt-based alloy, a nickel-titanium-based alloy or the like is generally used.

As a radiopaque marker, gold or platinum having a highly radiopaque property is generally used. Gold and platinum have extremely high electric potentials.

For this reason, the potential difference is increased between the metallic material used in the stent and gold or platinum used in the radiopaque marker causing the galvanic corrosion described above, thereby resulting in liquation of the less-noble metal.

Therefore, when the stent is placed in a living body for a long period, there is a possibility that the metal may liquate in a body fluid such as blood, thereby causing a safety problem.

In consideration of the above-described problem, JP-A-2002-263195 (corresponding to U.S. Patent Application Publication No. 2001/0001317) discloses that a radiopaque tab is provided at a stent by micro-alloying the radiopaque metallic material such as gold or platinum with a nickel-titanium-based alloy constituting the stent (See, for example, paragraph [0038] in JP-A-2002-263195).

According to the disclosure, there is no remarkable occurrence of a galvanic element (See, for example, paragraph [0016] in JP-A-2002-263195).

For example, according to JP-A-2002-263195 described above (corresponding to U.S. Patent Application Publication No. 2001/0001317), an infinitesimally small amount of radiopaque metallic material can be added to a metallic material (for example, nickel-titanium-based alloy) constituting a stent and as such a sufficient radiopaque property cannot be applied to the stent.

Therefore, when performing placement of the stent, a position of the stent cannot be favorably and visually confirmed through radioscopy.

Meanwhile, if the amount of radiopaque metallic material to be added to the metallic material constituting the stent is increased in order to enhance the radiopaque property, it is no longer in a micro-alloyed state causing frequent occurrences of phase separation or extraction. As a result, a potential difference (galvanic potential) can be generated between the metallic material configuring the stent and the radiopaque metallic material, thereby accelerating galvanic corrosion.

SUMMARY

In accordance with an exemplary embodiment, the present disclosure provides a stent having a marker which can secure the sufficient radiopaque property and help prevent galvanic corrosion from occurring.

In accordance with an exemplary embodiment, to solve the above-described issues, a radiopaque marker is disclosed that can be made of a complete solid solution alloy having an electric potential which is close to that of the metallic material constituting a stent main body to the stent main body.

In accordance with an exemplary embodiment, a stent is disclosed, which includes a stent main body that is made of a metal, and a radiopaque marker that is made of a complete solid solution alloy having a corrosion potential of ±200 mV of a corrosion potential of the metal.

In accordance with an exemplary embodiment, a stent is disclosed comprising: a stent main body that is made of a metal having a corrosion potential, wherein the stent main body is a cylindrical body in which both terminal portions are open, and which extends in a longitudinal direction between both of the terminal portions, and wherein the cylindrical body includes a plurality of annular units, each of the plurality of annular units includes a plurality of rhombus-shaped elements, which are continuously arranged and linked in a short axial direction of the plurality of rhombus-shaped elements; and at least one radiopaque marker that is made of a complete solid solution alloy having a corrosion potential, and wherein the at least one radiopaque marker is located within at least one of the plurality of annular units, and the corrosion potential of the radiopaque marker is ±200 mV of the corrosion potential of the metal of the stent main body.

In accordance with an exemplary embodiment, a method is disclosed of exhibiting radiopaque properties in a stent comprising: placing a radiopaque marker that is made of a complete solid solution alloy in a stent main body that is made of a metal, and wherein a corrosion potential of the radiopaque marker is ±200 mV of a corrosion potential of the metal of the stent main body.

DETAILED DESCRIPTION

The present disclosure relates to a stent including a stent main body that is made of a metal, and a radiopaque marker (hereinafter, simply referred to as "marker") that is made of a complete solid solution alloy having a corrosion potential of ±200 mV (plus or minus 200 mV) which is the corrosion potential of the metal (hereinafter, simply referred to as "complete solid solution alloy").

As described above, when metals of different types are brought into contact with each other and are immersed in an electrolyte solution, a potential difference (galvanic potential) can be generated between a less-noble metal (metal having greater ionization tendency) and a noble metal (metal having smaller ionization tendency) due to a difference in electric potential therebetween so that a battery (local battery, galvanic battery) is formed, and a current (local current) flows, thereby causing corrosion (galvanic corrosion).

As the potential difference is greater, the flowing current further increases, thereby accelerating corrosion.

To the contrary, when metallic materials respectively constituting the marker and the stent have substantially the same electric potentials, the galvanic corrosion does not occur theoretically.

Alloying of metals can be considered as means for adjusting the potential difference. However, if the alloying is performed alone, there are frequent occurrences of phase separation, extraction or the like as described above, thereby making it difficult to adjust the electric potential.

In contrast, in accordance with an exemplary embodiment, the radiopaque marker of the stent of the present disclosure is made of a complete solid solution alloy having the corrosion potential within a particular range with respect to the metallic material (metal) constituting the stent main body, and which is installed on the main body of the stent.

Here, the complete solid solution alloy constituting the radiopaque marker can have an electric potential (corrosion potential) which is close to that of the metal (for example, stainless steel and a Co-based alloy) constituting the main body of the stent.

In the stent of the present disclosure, since the potential difference between both of the metals is minimal, even though the radiopaque marker is brought into contact with the dissimilar metal (metal constituting stent main body), a local current scarcely flows in substance, and thus, the metal can be suppressed and can also help prevent the metal from liquating due to the galvanic corrosion.

In accordance with an exemplary embodiment, the radiopaque marker of the present disclosure can be made of a complete solid solution so that there is no occurrence of the phase separation, the extraction or the like even though the alloy composition is changed.

Therefore, the difference between the electric potential (corrosion potential) of the complete solid solution alloy and the electric potential (corrosion potential) of the metal can be easily adjusted within a particular range by adjusting the alloy composition of the complete solid solution alloy.

Accordingly, the stent of the present disclosure can be safely placed inside a living body lumen such as a blood vessel for a long period without causing galvanic corrosion.

Accordingly, the stent of the present disclosure can secure a sufficient radiopaque property and help prevent galvanic corrosion from occurring.

Therefore, the stent of the present disclosure can be favorably and visually confirmed through radioscopy and can be safely placed inside the living body lumen such as a blood vessel for a long period.

Throughout the present disclosure, the electric potential of the metal or the complete solid solution alloy is expressed as "corrosion potential".

In the present specification, the "corrosion potential" is measured through a method disclosed in JIS T0302: 2000. Specifically, the corrosion potential is a value (mV) measured by the method disclosed below.

Method of Measuring Corrosion Potential

A sample (sample made of metal or complete solid solution alloy) is cut into appropriate sized pieces.

In order to eliminate influence at the time of cutting the sample, the sample is abraded in running water using waterproof abrasive paper.

In this case, the sheets of abrasive paper are used starting with coarse grit (150 grit) and ending with 600 grit.

After the abrasion, the sample is subjected to ultrasonic cleaning in distilled water for five minutes.

After the cleaning, a lead wire is connected to the sample.

A method of connecting the sample and the lead wire is appropriately selected from soldering, applying of Dotite, clipping, screw-fastening and the like depending on the shape of the sample.

Subsequently, the sample including the portion connected to the lead wire is coated by a sealing agent so as to be exposed over only 1 square centimeter.

After the coating, the sample is subject to the following evaluation within 24 hours.

An electrolysis cell containing a PBS solution (composition: 8.0 g/L of NaCl, 0.2 g/L of KCl, 1.15 g/L of $Na_2HPO_4$, 0.2 g/L of $KH_2PO_4$, and pH 7.2 to pH 7.6) is inserted into a constant temperature bath, and the PBS solution is maintained at a temperature of 37° C.

The PBS solution is subjected to bubbling with high-purity nitrogen gas for 30 minutes or longer.

Thereafter, the previously prepared sample is immersed in the PBS solution.

The electric potential generated in the sample is measured with an electrometer (manufactured by Hokuto Denko Corporation, product name: HE-104).

The measurement is carried out in a state of being immersed at 37° C. for an hour, and a value measured after an hour is used as a corrosion potential (mV).

Hereinafter, an exemplary embodiment of the present disclosure will be described.

In the present disclosure, the stent main body can be made of a metal.

Here, the metal is not particularly limited so that it is possible to use a metal similar to what is used for a stent in the general medical field.

Specifically, for example, stainless steel, a cobalt-based alloy, a nickel-titanium-based alloy, tantalum, a tantalum-based alloy, platinum, a platinum-based alloy, gold, a gold-based alloy, molybdenum, a molybdenum-based alloy and the like can be exemplified.

After producing a shape of the stent using a material other than what is mentioned above, plating may be performed with the aforementioned metallic material.

After producing the final shape of the stent, it is preferable to perform annealing.

Softness and flexibility of the stent can be improved in its entirety by performing the annealing, thereby achieving favorable placeability inside a bent blood vessel.

Compared to a case of not performing the annealing, a force of the expanded stent intended to restore the shape before being expanded, and particularly a force which is manifested when the stent is expanded in a bent portion of a blood vessel intended to return to a linear state is weakened so that physical stimuli applied to a bent inner wall of the blood vessel are decreased, and thus, it is possible to minimize the factors of restenosis.

It is preferable to perform the annealing by heating the stent at 900° C. to 1,200° C. under an inert gas atmosphere (for example, an argon gas) or under a vacuum state followed by cooling the stent at a rate so as not to cause quench hardening and an intermetallic phase so as to help prevent the surface of the stent from being oxidized.

It is preferable to perform passivation treatment before or after producing the final shape of the stent.

A minute and thin oxide film is formed on the surface of the stent by performing the passivation treatment, and thus, corrosion (liquation) of the stent (metal), and particularly corrosion (liquation) of the stent (metal) in body fluid can be effectively suppressed and relatively prevented.

Here, for example, it is preferable that the metal constituting the stent main body be stainless steel, a cobalt-based alloy and a nickel-titanium-based alloy among the aforementioned materials.

Here, for example, stainless steel which is allowed to be used in the general medical field can be used in the same manner. For example, SS304, SS316L, SS420J2, SS630 and the like can be exemplified.

Among those, for example, for corrosion resistance and performance records inside a living body, it can be preferable to use SS316L (composition: carbon equal to or less than 0.035% by weight, phosphorus equal to or less than 0.04% by weight, sulfur equal to or less than 0.03% by weight, manganese equal to or less than 2.00% by weight, silicon equal to or less than 0.75% by weight, chromium from 16.00% by weight to 18.00% by weight, nickel from 12.00% by weight to 15.00% by weight, molybdenum from 2.00% by weight to 3.00% by weight, and iron for the remaining portion).

As the cobalt-based alloy, a cobalt-based alloy which is allowed to be used in the general medical field can be used in the same manner. For example, a cobalt-chrome alloy such as L605, a cobalt-nickel-chrome alloy, a cobalt-nickel-chrome-molybdenum alloy such as MP35N, a cobalt-chrome-molybdenum alloy and the like can be exemplified.

Among those, for example, for corrosion resistance, strength and performance records inside a living body, it can be preferable to use L605 (composition: chromium from 19.00% by weight to 21.00% by weight, nickel from 9.00% by weight to 11.00% by weight, tungsten from 14.00% by weight to 16.00% by weight, iron 3.00% by weight at the maximum, manganese from 1.00% by weight to 2.00% by weight, carbon from 0.05% by weight to 0.15% by weight, silicon 0.40% by weight at the maximum, phosphorus 0.040% by weight at the maximum, sulfur 0.030% by weight at the maximum, and cobalt for the remaining portion) and MP35N (composition: carbon 0.025% by weight at the maximum, phosphorus 0.015% by weight at the maximum, sulfur 0.010% by weight at the maximum, manganese 0.15% by weight at the maximum, silicon 0.15% by weight at the maximum, chromium from 19.00% by weight to 21.00% by weight, nickel from 33.00% by weight to 37.00% by weight, molybdenum from 9.00% by weight to 10.50% by weight, titanium 1.00% by weight at the maximum, boron 0.01% by weight at the maximum, iron 1.00% by weight at the maximum, and cobalt for the remaining portion).

As the nickel-titanium-based alloy, a nickel-titanium-based alloy which is allowed to be used in the general medical field can be used in the same manner. For example, a nickel-titanium alloy in which nickel is contained approximately 50% by weight to approximately 60% by weight and titanium fills the remaining portion, and a nickel-titanium-copper alloy in which copper is added to the nickel-titanium alloy can be exemplified.

Among those, for example, from the point of view of performance records inside a living body, corrosion resistance and a superelastic characteristic, it is preferable to use the aforementioned nickel-titanium alloy (nitinol) in which nickel is contained approximately 50% by weight to approximately 60% by weight and titanium fills the remaining portion.

In accordance with an exemplary embodiment, the aforementioned metals may be used individually (only one type) to constitute the stent main body or may be used as a mixture of two or more types to constitute the stent main body. However, it can be preferable to use the metal individually to constitute the stent main body.

In the present disclosure, the radiopaque marker is made of a complete solid solution alloy.

The complete solid solution alloy can be made of a complete solid solution so that there is no occurrence of the phase separation, the extraction or the like, even though the alloy composition can be changed.

Therefore, in accordance with an exemplary embodiment, the difference between the electric potential (corrosion potential) of the complete solid solution alloy and the electric potential (corrosion potential) of the metal can be easily adjusted within the particular range by adjusting the alloy composition of the complete solid solution alloy.

The complete solid solution alloy has the radiopaque property.

Here, the term "radiopaque" denotes that the marker is enough to be visually confirmed through the radioscopy at a general medical site.

In the present disclosure, density is used as an indicator of the radiopaque property. Generally, for example, as the density is higher, the radiopaque property of the marker is higher.

From a point of view of the marker to be visually confirmed through the radioscopy at a general medical site, it can be preferable for the complete solid solution alloy to have a density equal to or higher than 10 g/cm$^3$, and more preferable to have a density equal to or higher than 12 g/cm$^3$.

When the complete solid solution alloy has such density (relative density), the marker can exhibit a sufficient radiopaque property so as to be able to be sufficiently and visually confirmed through the radioscopy.

In accordance with an exemplary embodiment, the complete solid solution alloy has a corrosion potential of ±200 mV which is the corrosion potential of the metal.

The expression "the complete solid solution alloy has a corrosion potential of ±200 mV which is the corrosion potential of the metal" denotes that the absolute value of the difference between the corrosion potentials of the metal and the complete solid solution alloy is equal to or less than 200 mV, that is, the corrosion potential of the complete solid solution alloy is within a range from "corrosion potential of metal −200 mV" to "corrosion potential of metal +200 mV".

When the absolute value is within such a range, even though the complete solid solution alloy is brought into contact with the metal and is in a body fluid such as blood, since the potential difference therebetween is minimal, the stent can sufficiently help prevent corrosion (galvanic corrosion) from occurring.

It is better for the corrosion potential of the complete solid solution alloy to be ±200 mV with respect to the corrosion potential of the metal. However, it is preferable that the corrosion potential of the complete solid solution alloy be as close as possible to the corrosion potential of the metal.

Therefore, with respect to the corrosion potential of the metal, the corrosion potential of the complete solid solution alloy, for example, is preferably ±150 mV, is more preferably ±130 mV, is still more preferably ±120 mV, and is particularly preferably ±110 mV.

The aforementioned complete solid solution alloy may be constituted with any metal without being particularly limited as long as the alloy is made of the complete solid solution, has a radiopaque property, and has the corrosion potential of ±200 mV with respect to the corrosion potential of the metal.

Specifically, for example, it is preferable that the complete solid solution alloy be constituted with metals of at least two types which are selected from a group including molybdenum (Mo), tantalum (Ta), niobium (Nb), tungsten (W), vanadium (V), cobalt (Co), palladium (Pd), nickel (Ni) and rhodium (Rh).

Combinations of those metals are not particularly limited as long as the combinations form complete solid solutions, thereby being exemplified such as Mo—Ta, Nb—W, Ta—W, Mo—W, Nb—Ta, V—W, Co—Pd, Mo—Nb, Mo—V, Ni—Pd, Ni—Rh and Nb—V.

Among those, Mo—Ta, Nb—W, Ta—W, Mo—W, Nb—Ta, V—W, Co—Pd, Mo—Nb, Mo—V, Ni—Pd and Ni—Rh can be preferable.

As long as the complete solid solution alloy is made of the complete solid solution, has a radiopaque property, and has the corrosion potential of ±200 mV with respect to the corrosion potential of the metal, the metals may be used individually (only one type) to constitute the marker or may be used as a mixture of two or more types to constitute the marker. However, for example, it is preferable to use the metals individually to constitute the marker.

The composition of the complete solid solution alloy is not particularly limited as long as the alloy is made of the complete solid solution, has a radiopaque property, and has the corrosion potential of ±200 mV with respect to the corrosion potential of the metal. The composition can be appropriately selected depending on the metal constituting the stent main body.

For example, when the metal is passivated L605, 75 Mo-25 Ta, 50 Mo-50 Ta, 50 Nb-50 W, 25 Nb-75 W and 50 Ta-50 W (each number indicates % by mole, adding up 100% by mole in total) are preferable.

When the metal is passivated SS316L, 75 Mo-25 Ta, 50 Mo-50 Ta, 50 Nb-50 W, 25 Nb-75 W and 50 Ta-50 W (each number indicates % by mole, adding up 100% by mole in total) are preferable.

It is allowable for the complete solid solution alloy to contain other unavoidable impurities (unavoidable elements of impurities) derived from the raw material of the complete solid solution alloy.

The unavoidable impurity is a component acknowledged to be unnecessary as it is not an essential component for constituting the alloy, and is an impurity unavoidably mixed in the alloy through a raw material of the alloy component or a processing step.

The unavoidable impurity content is not particularly limited as long as the content is such that the alloy is not critically affected. However, it is preferable that the total amount be equal to or less than 0.3% by mole.

The stent of the present disclosure has the stent main body made of metal and the radiopaque marker made of a particular complete solid solution alloy.

As the stent of the present disclosure, a stent similar to the stents used in the related art can be used.

The stent of the present disclosure may be any one of a balloon-expandable stent (balloon expansion-type stent) and a self-expandable stent (self-expansion-type stent).

The shape of the stent is not particularly limited as long as the stent has a stent main body and a marker. However, it is preferable to have strength enough to be stably placed inside a living body lumen such as a blood vessel.

For example, a cylindrical shape formed by weaving a fiber or a tubular body provided with an opening portion can be favorably exemplified.

Figure 1:
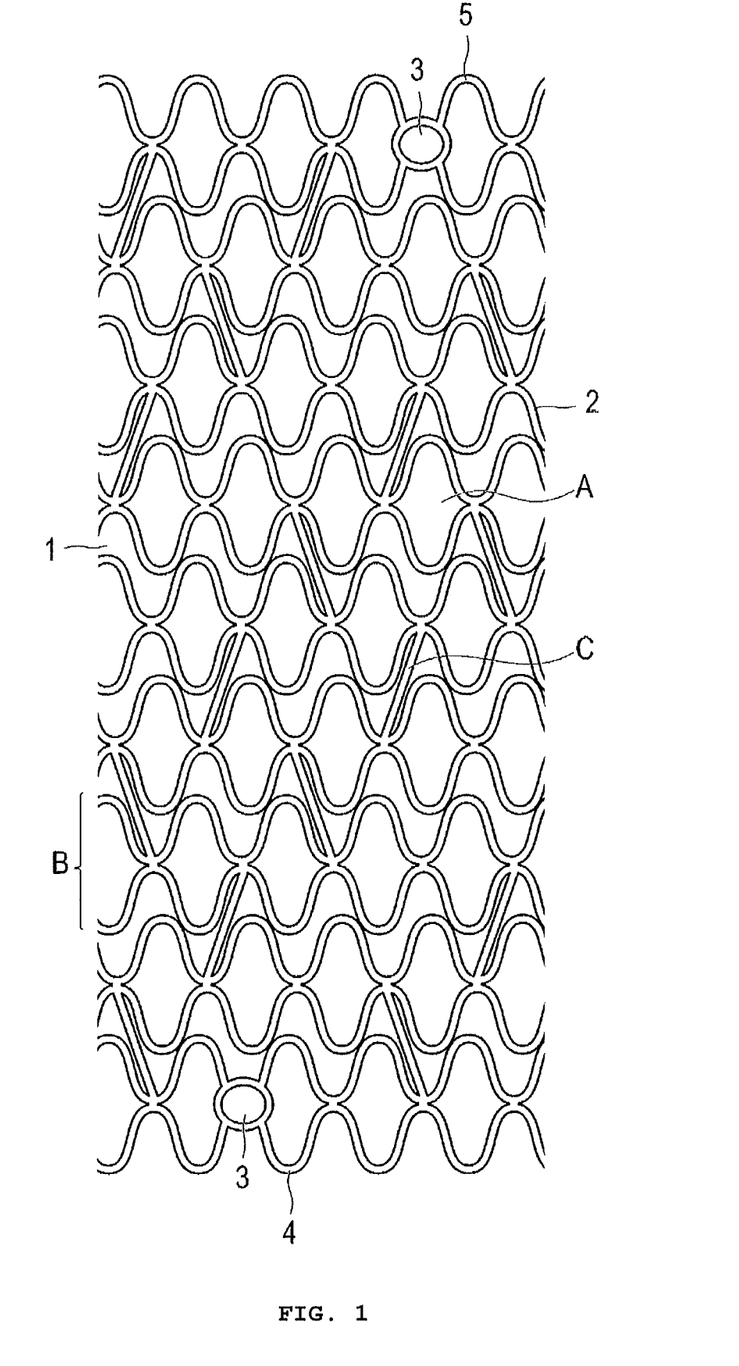
FIG. 1 is a view illustrating a stent according to an exemplary embodiment of the present disclosure.
Figure 2:
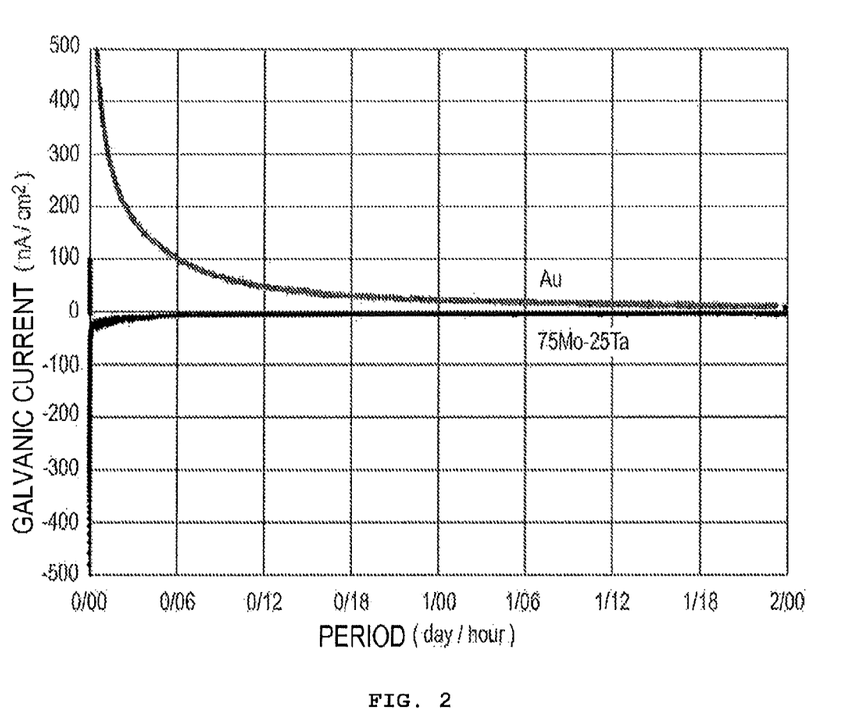
FIG. 2 is a view illustrating galvanic currents ($nA/cm^2$) of 75 Mo-25 Ta and Au in exemplary embodiment 1.
Figure 3:
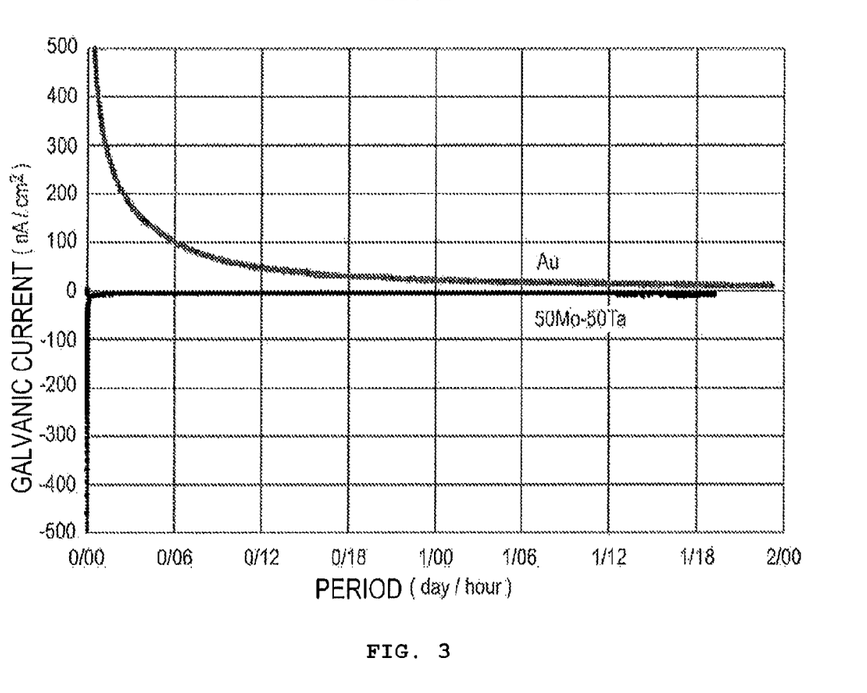
FIG. 3 is a view illustrating galvanic currents ($nA/cm^2$) of 50 Mo-50 Ta and Au in exemplary embodiment 1.
Figure 4:
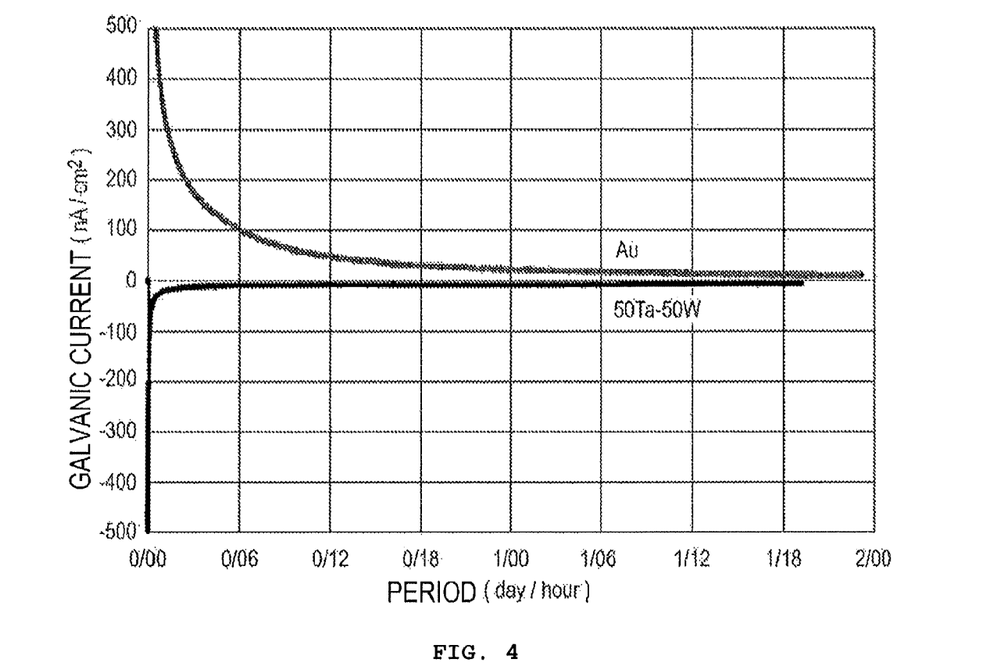
FIG. 4 is a view illustrating galvanic currents ($nA/cm^2$) of 50 Ta-50 W and Au in exemplary embodiment 1.
Figure 5:
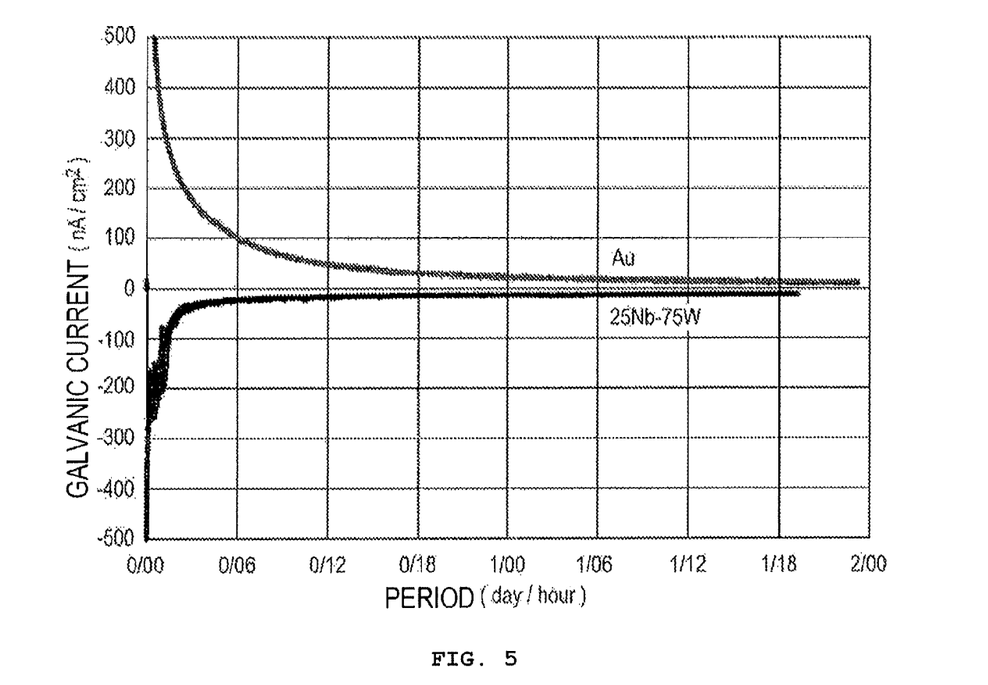
FIG. 5 is a view illustrating galvanic currents ($nA/cm^2$) of 25 Nb-75 W and Au in exemplary embodiment 1.

For example, as an example of the balloon expandable stent, in a stent 1 illustrated in FIG. 1, a stent main body 2 is a cylindrical body in which both of terminal portions are open, and which extends in a longitudinal direction between both of the terminal portions.

A side surface of the cylindrical body can have multiple notch portions allowing an outer side surface and an inner side surface of cylindrical body to communicate with each other. The cylindrical body is structured to be able to expand and contract in a radial direction of the cylindrical body in response to deformation of the notch portion, and is placed inside a living body lumen such as a blood vessel, thereby maintaining the shape of the cylindrical body.

In the exemplary embodiment illustrated in FIG. 1, a substantially rhombus-shaped element A having a notch portion inside of the substantially rhombus-shaped element is a base unit of the stent (main body).

The plurality of elements A having the substantially rhombus shapes form an annular unit B in which the shapes of the substantial rhombus shapes (or lozenge) are continuously arranged and linked in a short axial direction of the substantial rhombus shapes.

The annular unit B is connected to the adjacent annular unit via a line-shaped connection member C.

Accordingly, the plurality of annular units B can be in states of being partially linked to each other and continuously arranged in the axial direction of plurality of annular units.

According to such a configuration, the stent (main body) is the cylindrical body in which both of the terminal portions are open and which extends in the longitudinal direction between both of the terminal portions.

The side surface of the cylindrical body has the substantially rhombus-shaped notch portions and can be structured to be able to expand and contract in the radial direction of the cylindrical body in response to deformation of the notch portions.

However, the structure of the stent in the present disclosure is not limited to the illustrated embodiment in the drawing. The concepts disclosed herein can include structures of a stent that are a cylindrical body in which both of terminal portions are open, which extends in the longitudinal direction between both of the terminal portions, which has multiple notch portions on its side surface allowing an outer side surface and an inner side surface to communicate with each other, and which can expand and contract in the radial direction of the cylindrical body in response to deformation of the notch portions. A coil shape is included in the concept of the present disclosure as well.

Regarding a shape of a cross section of a wire configuring the stent (main body), the shape may be different such as a rectangular shape, a circular shape, an oval shape and other polygonal shapes.

In addition to the above description, as another preferable example of the stent 1, there is a stent having a lattice-shaped structure.

A radiopaque marker 3 may be arranged at any position in the stent main body. However, it is preferable to be provided at an end portion of the stent main body 2, and it is more preferable to be respectively provided at both of the end portions of the stent main body 2 as illustrated in FIG. 1.

For example, it is preferable to provide one radiopaque marker 3 in the annular unit B at one end side (specifically, for example, a tip (distal end) 4 side) of the stent main body and another radiopaque marker 3 in the annular unit B at the other end side (specifically, for example, a proximal end 5 side).

Accordingly, the positions of both the end portions of the stent can be easily confirmed.

Besides the above description, the stents disclosed in JP-A-2002-263195 (particularly, FIGS. 9 and 10), JP-A-2004-121342 (particularly, FIG. 6), JPA-2004-290279 (particularly, FIGS. 6 and 7), JP-A-2005-278993, Specification of U.S. Pat. No. 6,402,777 (particularly, FIG. 1) and the like can be applied in a similar manner or after being appropriately modified.

In detail, for example, the markers 200 and 300 illustrated in FIGS. 9 and 10 in JP-A-2002-263195 can be made of the complete solid solution alloy, thereby being mounted on the stent main body.

Figure 6:
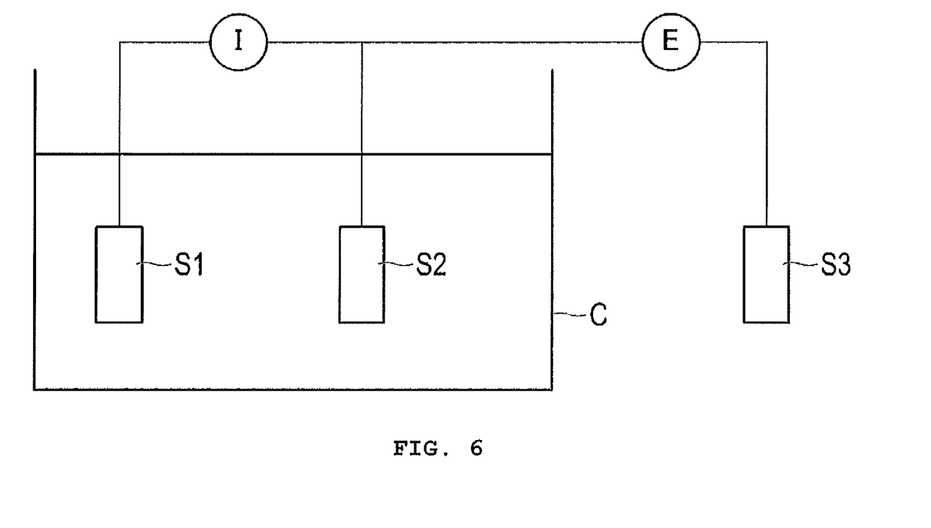
FIG. 6 is a view illustrating an apparatus for measuring the galvanic current in exemplary embodiment 1.

The small opening 51 formed in the stent 1 illustrated in FIG. 6 of JPA-2004-121342 can be blocked by the complete solid solution alloy and the alloy can be fixed to the stent.

The rivet disclosed in Specification of U.S. Pat. No. 6,402,777 can be made of the complete solid solution alloy.

The size of the stent main body is not particularly limited. The size may be appropriately selected in accordance with a part to be applied.

The outer diameter of the stent before being expanded is preferably approximately 0.3 mm to 5 mm, is more preferably approximately 0.4 mm to 4.5 mm, and is particularly preferably approximately 0.5 mm to 1.6 mm.

The length of the stent is not particularly limited as well. The length can be appropriately selected in accordance with a disease to be treated.

For example, the length of the stent is preferably approximately 5 mm to 100 mm, and is more preferably approximately 6 mm to 50 mm.

The length of the stent is preferably approximately 1.5 mm to 4 mm, and is more preferably approximately 2 mm to 3 mm, for example.

The thickness of the stent is not particularly limited as long as the thickness has a radial force necessary to be placed in a stenosed part and is such that a blood flow is not inhibited. However, the thickness is preferably in a range from 1 μm to 1,000 μm, and is more preferably in a range from 50 μm to 300 μm, for example.

The size of the radiopaque marker is not particularly limited. The size may be appropriately selected in accordance with a part to be applied.

For example, as illustrated in FIG. 1, or FIG. 10 in JP-A-2002-263195, when the marker has a circular shape, the diameter of the radiopaque marker is preferably approximately 0.01 mm to 0.7 mm, and is more preferably approximately 0.02 mm to 0.5 mm.

As illustrated in FIG. 9 in JP-A-2002-263195, when the marker has a rectangular shape, the size of the radiopaque marker is preferably approximately 0.01 mm to 0.7 mm×0.01 mm to 0.7 mm, and is more preferably approximately 0.02 mm to 0.5 mm×0.02 mm to 0.5 mm.

At such a size, the radiopaque marker can be sufficiently and visually confirmed through the radioscopy.

Thus, the position of the stent can be favorably and visually confirmed through the radioscopy.

An effect of the present disclosure will be described with reference to the following examples.

However, the technical range of the present disclosure is not limited to only the following examples.

REFERENCE EXAMPLE 1

The alloys (complete solid solution alloy) including 75 Mo-25 Ta, 50 Mo-50 Ta, 50 Nb-50 W, 25 Nb-75 W and 50 Ta-50 W are individually produced.

In the above description, each composition is expressed in % by mole.

Corrosion potentials of the alloys are measured, and the result is shown in Table 1 below.

The measurement of the corrosion potential is also performed in SS316L, a metal constituting a commercially available stent (Nobori®, manufactured by Terumo Corporation) and L605 (Co—Cr alloy), a metal constituting another commercially available stent (Kaname®, manufactured by Terumo Corporation), and the results are respectively −90.80 mV and −110.75 mV.

The differences between the corrosion potentials of the alloys and the corrosion potentials of SS316L or L605 are shown together in Table 1 below.

TABLE 1

|  | Corrosion Potential (mV v.s. SCE, PBS, 37° C.) | Difference between Corrosion Potentials | |
| --- | --- | --- | --- |
|  |  | SUS316L | L605 |
| 75Mo—25Ta | −217.68 | 126.9 | 106.9 |
| 50Mo—50Ta | −195.30 | 104.5 | 84.6 |
| 50Nb—50W | −191.85 | 101.1 | 81.1 |
| 25Nb—75W | −227.29 | 136.5 | 116.5 |
| 50Ta—50W | −200.74 | 109.9 | 90.0 |
| Au | 122.57 | 213.4 | 233.3 |
| SUS316L | −90.80 | — | — |
| L605 | −110.75 | — | — |

According to Table 1 above, regarding all the complete solid solution alloys including 75 Mo-25 Ta, 50 Mo-50 Ta, 50 Nb-50 W, 25 Nb-75 W and 50 Ta-50 W of the present disclosure, the absolute values of the differences between the corrosion potentials with respect to SS316L or L605, which is a metal generally constituting a stent are equal to or less than 200 mV, and thus, in the aforementioned alloys the occurrence of the galvanic corrosion (liquation of complete solid solution alloy) can be relatively prevented.

In contrast, for example, gold (Au), the absolute value of the difference between the corrosion potentials with respect to SS316L or L605 exceeds 200 mV, and thus, in gold the occurrence of the galvanic corrosion (liquation of stent main body) cannot be relatively prevented.

Exemplary Embodiment 1

The alloys (complete solid solution alloy) including 75 Mo-25 Ta, 50 Mo-50 Ta, 50 Ta-50 W and 25 Nb-75 W are individually produced.

In the above description, each composition is expressed in % by mole.

Regarding the aforementioned alloys, a galvanic current is measured using the apparatus in FIG. 6 through the following method.

The result is illustrated in FIGS. 2 to 5.

That is, samples (samples made of complete solid solution alloy and gold) are cut into appropriate sized pieces (2 cm×2 cm).

After the cutting, the samples are abraded in running water using waterproof abrasive paper.

In this case, the sheets of abrasive paper are used starting with coarse grit (150 grit) and ending with 600 grit.

After the abrasion, the sample is subjected to ultrasonic cleaning in distilled water for five minutes.

After the cleaning, a lead wire is connected to the sample by a clip.

Subsequently, the sample including the portion connected to the lead wire is coated by a sealing agent so as to be exposed over only 1 square centimeter.

That is used as a sample pole (electrode S2).

Similarly, L605 (Co—Cr alloy), the metal constituting a commercially available stent (Kaname®, manufactured by Terumo Corporation) is connected to a lead wire and coated by the sealing agent in a manner similar to the above case, thereby be used as the counter pole (electrode S1).

After the coating, the sample is subject to the following evaluation within 24 hours.

In this case, as a reference pole (standard electrode), Ag/AgCl electrode (silver/silver chloride electrode) S3 is used, and the electrometer ("E" in FIG. 6) is installed between the reference pole S3, and the electrodes S1 and S2.

A cell C containing the PBS solution (composition: 8.0 g/L of NaCl, 0.2 g/L of KCl, 1.15 g/L of $Na_2HPO_4$, 0.2 g/L of $KH_2PO_4$, and pH 7.2 to pH 7.6) is inserted into a constant temperature bath (not illustrated), and the PBS solution is maintained at a temperature of 37° C.

The PBS solution is subjected to bubbling with high-purity nitrogen gas for 30 minutes or longer.

Thereafter, the previously prepared electrodes S1 and S2 are immersed in the PBS solution.

A current flowing between the counter pole (electrode S1) and the sample pole (electrode S2) is measured by a zero shunt ammeter ("I" in FIG. 6).

In this case, the measurement temperature is adjusted to be 37° C.

As illustrated in FIGS. 2 to 5, in the alloys (complete solid solution alloy) including 75 Mo-25 Ta, 50 Mo-50 Ta, 50 Ta-50 W and 25 Nb-75 W, there are few occurrences or no occurrence of the galvanic current (local current) with respect to L605 which is a metal generally constituting a stent.

From that fact, it is considered that a stent having a radiopaque marker made of a complete solid solution alloy according to the present disclosure can be safely placed inside a living body lumen for a long period, without causing the galvanic corrosion even after being placed inside the living body lumen (for example, blood vessel).

In contrast, regarding gold which has a large potential difference with respect to the corrosion potential of the metal (L605) constituting the stent main body, the galvanic current (local current) is generated with respect to L605, and thus, it is learned that there is an occurrence of corrosion (liquation) of the stent main body.

From FIGS. 2 to 5, for example, in the case of gold, the galvanic current of gold is large immediately after the immersion but gradually decreases.

However, even in such a case, corrosion proceeds from a crevice (crevice corrosion) of a portion (connection portion of stent main body and radiopaque marker) where the corrosion (liquation) occurs, the corrosion (liquation) of the stent main body can proceed even after the galvanic current is lowered.

The detailed description above describes embodiments of a stent disclosed by way of example. The disclosure is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent comprising:
    a stent main body that is made of a metal, wherein the metal of the stent main body is a cobalt-based alloy; and
    a radiopaque marker that is made of a complete solid solution alloy having a corrosion potential of ±200 mV of a corrosion potential of the metal of the stent main body, wherein the complete solid solution alloy is 75 Mo-25 Ta, 50 Mo-50 Ta, 50 Nb-50 W, 25 Nb-75 W, or 50 Ta-50 W, wherein each number indicates % by mole, adding UP 100% by mole in total.

2. The stent according to claim 1,
    wherein the corrosion potential of the complete solid solution alloy is ±150 mV with respect to the corrosion potential of the metal.

3. The stent according to claim 1,
    wherein the stent is a balloon-expandable stent or a self-expandable stent.

4. The stent according to claim 1,
wherein the stent main body is a cylindrical body in which both terminal portions are open, and wherein the cylindrical body extends in a longitudinal direction between both of the terminal portions.

5. The stent according to claim 4,
wherein a side surface of the cylindrical body has multiple notch portions forming an outer side surface and an inner side surface, which are configured to communicate with each other.

6. The stent according to claim 5,
wherein the cylindrical body is structured to expand and contract in a radial direction of the cylindrical body in response to deformation of the notch portions, and is configured to be placed inside a blood vessel of a living body lumen.

7. The stent according to claim 5,
wherein the cylindrical body includes a plurality of rhombus-shaped elements, which form an annular unit in which the plurality of rhombus-shaped elements are continuously arranged and linked in a short axial direction of the plurality of rhombus-shaped elements.

8. The stent according to claim 7, comprising
a plurality of adjacent annular units, which are connected via one or more line-shaped connection members.

9. The stent according to claim 1,
wherein the radiopaque marker is provided at an end portion of the stent main body.

10. The stent according to claim 9,
wherein radiopaque markers are provided at both end portions of the stent main body.

11. A stent comprising:
a stent main body that is made of a metal, wherein the metal of the stent main body is stainless steel; and
a radiopaque marker that is made of a complete solid solution alloy having a corrosion potential of ±200 mV of a corrosion potential of the metal of the stent main body, wherein the complete solid solution alloy is 75 Mo-25 Ta, 50 Mo-50 Ta, 50 Nb-50 W, 25 Nb-75 W, or 50 Ta-50 W, wherein each number indicates % by mole, adding up 100% by mole in total.

12. The stent according to claim 11,
wherein the corrosion potential of the complete solid solution alloy is ±150 mV with respect to the corrosion potential of the metal.

13. The stent according to claim 11,
wherein the stent is a balloon-expandable stent or a self-expandable stent.

14. The stent according to claim 11,
wherein the stent main body is a cylindrical body in which both terminal portions are open, and wherein the cylindrical body extends in a longitudinal direction between both of the terminal portions.

15. The stent according to claim 14,
wherein a side surface of the cylindrical body has multiple notch portions forming an outer side surface and an inner side surface, which are configured to communicate with each other.

16. A stent comprising:
a stent main body that is made of a metal having a corrosion potential, wherein the metal of the stent main body is a cobalt-based alloy, and wherein the stent main body is a cylindrical body in which both terminal portions are open, and which extends in a longitudinal direction between both of the terminal portions, and wherein the cylindrical body includes a plurality of annular units, each of the plurality of annular units includes a plurality of rhombus-shaped elements, which are continuously arranged and linked in a short axial direction of the plurality of rhombus-shaped elements; and
at least one radiopaque marker that is made of a complete solid solution alloy having a corrosion potential, and wherein the at least one radiopaque marker is located within at least one of the plurality of annular units, and the corrosion potential of the radiopaque marker is ±200 mV of the corrosion potential of the metal of the stent main body, wherein the complete solid solution alloy is 75 Mo-25 Ta, 50 Mo-50 Ta, 50 Nb-50 W, 25 Nb-75 W, or 50 Ta-50 W, wherein each number indicates % by mole, adding UP 100% by mole in total.

17. A method of exhibiting radiopaque properties in a stent comprising:
placing a radiopaque marker that is made of a complete solid solution alloy in a stent main body that is made of a metal, and wherein a corrosion potential of the radiopaque marker is ±200 mV of a corrosion potential of the metal of the stent main body, wherein the metal of the stent main body is a cobalt-based alloy, and wherein the complete solid solution alloy is 75 Mo-25 Ta, 50 Mo-50 Ta, 50 Nb-50 W, 25 Nb-75 W, or 50 Ta-50 W, wherein each number indicates % by mole, adding up 100% by mole in total.

* * * * *